United States Patent [19]

Guerrato et al.

[11] 4,362,891
[45] Dec. 7, 1982

[54] ALKANOIC ACID DERIVATIVES

[75] Inventors: Alfredo Guerrato; Michele Perchinunno, both of Verona, Italy

[73] Assignee: Glaxo Group Limited, London, England

[21] Appl. No.: 160,426

[22] Filed: Jun. 17, 1980

[30] Foreign Application Priority Data

Jun. 18, 1979 [GB] United Kingdom ............... 7921083

[51] Int. Cl.³ ..................... C07C 63/64; C07C 69/76
[52] U.S. Cl. ........................................ 562/495; 560/9; 560/17; 560/55; 560/61; 562/426; 562/471; 562/465; 260/501.1; 424/308; 424/316
[58] Field of Search ..................... 562/495; 560/104; 424/308, 316

[56] References Cited

U.S. PATENT DOCUMENTS

| 3,385,886 | 5/1968 | Nicholson et al. | |
| 3,385,887 | 5/1968 | Nicholson et al. | |
| 3,397,225 | 8/1968 | Fenton | 560/104 |
| 3,649,668 | 3/1972 | Dolinski | 560/104 |
| 3,652,608 | 3/1972 | Fenton | 560/104 |
| 3,729,509 | 4/1973 | Schultz | 560/104 |
| 3,959,364 | 5/1976 | Armitage et al. | |

FOREIGN PATENT DOCUMENTS 1012480 12/1965 United Kingdom .

Primary Examiner—Paul J. Killos
Attorney, Agent, or Firm—Bacon & Thomas

[57] ABSTRACT

An alkanoic acid compound is disclosed of formula:

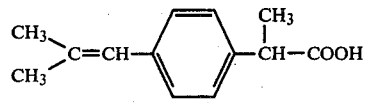

and certain of its physiologically acceptable salts and esters. The alkanoic acid compound and its salts and esters have an unexpectedly greater anti-inflammatory activity than representative members of a broad class of compounds, phenyl alkane derivatives, known to have therapeutic properties. The alkanoic acid compound also has unexpectedly high antipyretic and analgesic activity. The compounds may be formulated in conventional manner as pharmaceutical compositions.

The compound may be prepared from 2-[4-(1-hydroxy-2-dimethylethyl)phenyl] propionic acid directly by dehydration or via an ester by dehydration in the presence of an alkanol followed by hydrolysis.

12 Claims, No Drawings

ALKANOIC ACID DERIVATIVES

This invention relates to alkanoic acid derivatives more particularly to a 2-(4-alkenylphenyl) alkanoic acid compound its salts and esters, processes for their preparation and their uses.

A class of compounds consisting of phenyl alkane derivatives is known to have therapeutic properties. This class of compounds includes within its scope, inter alia, compounds of the general formula (I)

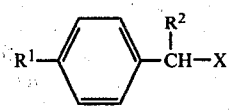

wherein $R^1$ represents ethyl, propyl, butyl, alkenyl ($C_2$-$C_4$), pentyl (except n-pentyl), alkoxy ($C_2$-$C_3$), allyloxy, phenoxy, phenylthio or cycloalkyl ($C_5$-$C_7$) optionally substituted by methyl or ethyl in the 1-position, $R^2$ represents hydrogen or methyl and X represents the radical COOH, $COOR^3$ wherein $R^3$ represents alkyl ($C_1$-$C_8$) or optionally N-alkylated aminoalkyl ($C_2$-$C_8$), COOM wherein M represents the ammonium ion or a single equivalent of a non-toxic metallic cation, COOH.B wherein B represents a non-toxic organic base, $CONH_2$, $CH_2NH_2$ or the group $CH_2OR^4$ where $R^4$ represents hydrogen or lower alkanoyl ($C_1$-$C_3$).

These phenyl alkane derivatives are known to have anti-inflammatory activity.

We have now found a compound which falls within this class of phenyl alkane derivatives which has surprisingly good therapeutic properties and, in particular, good anti-inflammatory activity as well as marked antipyretic and analgesic activity.

Thus, the present invention provides 2(4-dimethylvinylphenyl)propionic acid of formula (II):

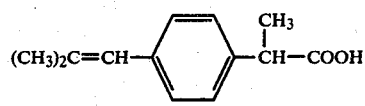

and its physiologically acceptable "salts" (as herein defined) and "esters" (as herein defined).

The physiologically acceptable "salts" are defined herein as the alkali and alkaline earth metal salts, particularly the sodium and calcium salts and the lysine, arginine and N-methyl-glucamine salts.

The physiologically acceptable "esters" are defined herein as the $C_{1-4}$ alkyl esters, particularly methyl or ethyl, or a $C_{2-5}$ alkanoyloxy methyl ester such as pivaloyloxy methyl or acetoxymethyl.

Preferred compounds according to the invention are the free acid of formula II, the calcium salt and the DL-lysine salt.

The acid of formula (II) and esters thereof may be prepared by dehydration of the compound of formula (III):

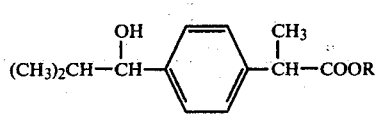

wherein R represents a hydrogen atom or a $C_1$-$C_4$ alkyl group or an alkanoyloxymethyl group.

The dehydration may conveniently be effected using p-toluene sulphonic acid or a derivative thereof, for example, p-toluene sulphonyl chloride or sulphuric acid in a high boiling, inert solvent such as toluene or halobenzenes for example dichlorobenzene, at elevated temperature.

In a modification of this process, the compound of general formula (III) in which R=H, may be dehydrated as just described but with the addition of a $C_1$-$C_4$ alkanol, for example methanol or ethanol, to produce an ester of the general formula (IV):

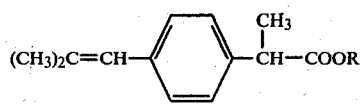

where R is a $C_1$-$C_4$ alkyl group.

The ester (IV) can be hydrolysed by conventional techniques to produce the acid (II). For example, the ester (IV) may be treated with a base, for example, sodium or potassium hydroxide, preferably at an elevated temperature.

The compounds of general formula (III) used as intermediate for the preparation of the compounds of formula (II) may be produced by reduction of the isobutyryl compound of formula (V):

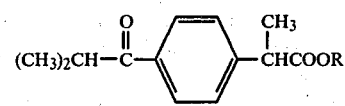

where R is as previously defined followed by hydrolysis where appropriate.

The reduction may be performed with a reducing agent, such as sodium borohydride, or by catalytic hydrogenation for example using platinum, palladium or Raney nickel.

The 2-(4-isobutyrylphenyl)propionic acid starting material of formula (V) in which R=H may be prepared by reacting a 4-isobutyrylhalobenzene of general formula (VI):

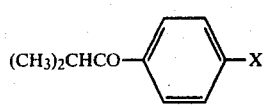

where X is a halogen atom, e.g. fluorine, with a dialkylmethylmalonate of general formula (VII):

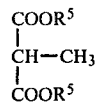

where $R^5$ is a $C_1$-$C_6$ alkyl group.

The malonate of general formula (VII) may be reacted in the form of an alkali metal salt, preferably the sodium salt.

This reaction is followed by hydrolysis and decarboxylation where necessary. Hydrolysis may be carried out under alkaline conditions followed by acidification or under acidic conditions.

Another possibility of preparing the compound of formula (III) is to hydrolyse with a base such as sodium hydroxide the product of the reaction of a compound of formula (VI) with a compound of formula (VII) followed by reduction of the basic hydrolysis product in the presence of a reducing agent preferably sodium borohydride, or by catalytic hydrogenation for example using platinum palladium or Raney nickel.

The 4-isobutyrylhalobenzene of general formula (VI) may be prepared, for example, by a conventional Friedel-Crafts reaction between an isobutyrylhalide and a halobenzene in the presence of, for example, aluminium trichloride.

The physiologically acceptable salts and esters of the compound of formula (II) may be prepared by conventional methods from the acid of formula (II). Thus salts may be prepared by treating the acid of formula II with a suitable base in the presence of a solvent such as water or aqueous acetone or water and an alkanol eg ethanol. Alkyl esters may be prepared from the reaction of the acid with a $C_1$–$C_4$ alkanol in the presence of a suitable acid catalyst eg concentrated sulphuric acid or a sulphonic acid eg p-toluene sulphonic acid.

Alternatively esters may be prepared by treating a salt of the acid (II) with an appropriate alkyl halide or alkanoyloxymethyl halide in a suitable solvent e.g. toluene.

The compound of formula II (and its "salts" (as herein defined) and "esters" (as herein defined) have an anti-inflammatory activity which is unexpectedly greater than that of its nearest known analogues belonging to the class of phenyl alkane derivatives referred to above, namely 2-(4-isobutylphenyl)propionic acid (ibuprofen) and 2-(4-methylvinylphenyl)propionic acid. The free acid also has an unexpectedly higher antipyretic and analgesic activity than the latter compound.

The following tests were performed to determine the anti-inflammatory activity of the compound (II).

1. Carrageenan Induced Edema in the Rat

A modification of the method described by C. A. Winter et al. (Proc.Soc.Exp.Biol.Med., 111, 544, 1962) was followed, using groups of female CD-COBS rats Charles River) of 150–170 g.

The compounds, suspended in 0.5% gum acacia, were orally administered in a fixed volume of 10 ml/KG. One hour later the inflammation was induced injecting 0.1 ml of a 1% suspension of carrageenan in 0.9 NaCl solution into the subplantar tissue of the right hindpaw of each rat. The paw volume was measured by means of a mercury displacement device supplied by U. Basile (Milano) at 0 time and again 3 hours after the carrageenan injection.

Edema volume was calculated as the difference between the paw volume after and before the induction of inflammation.

Percentage inhibition of the edema was calculated for each group as compared with control groups and statistical analysis was performed by means of the Dunnett test.

2. Freund Adjuvant Arthritis

Adjuvant arthritis (Pearson, C. M., Proc. Soc.Exp.Biol.Med., 91, 95, 1956) was induced in female rats weighing 150–175 g by intradermal injection into the tail of 0.1 ml of a fine suspension of *Mycobacterium butyricum* in liquid paraffin (6 mg/ml).

After 14 days animals were chosen on the basis of their arthritic score and groups of 5 rats were made. Test compounds, suspended in gum acacia, were orally administered once a day for 14 days; at the end of this period animals were scored again and percentage inhibition versus first score was calculated. Comparisons with controls were performed by the Dunnett test.

Analgesic activity was determined by the Randall-Selitto test.

In this test analgesic activity in rats was evaluated applying to the inflamed paw an increasing pressure (Randall, L. O., Selitto, J. J., Arch.int. Pharmacodyn., 111, 409, 1957) and recording pain threshold by means of an analgesimeter. Groups of 6 female CD-COBS rats were used for the experiment. Drugs were administered orally two hours after the injection of 0.1 ml of a 7.5% suspension of brewer's yeast into the plantar tissue of the right hind paw. Pain threshold was measured immediately before treatment and again two hours later and results were expressed as pain threshold increase in comparison with a control group. (Dunnett test).

Antipyretic activity was determined by the Yeast induced pyrexia test in rats.

This test was performed according to the method of Niemegeers et al. (Arzneim. Forsch., 25, 10, 1519, 1975), using female CD-COBS rats (Charles River, Italy) of 150–160 g. Pyrexia was induced injecting 15 ml/kg of a 20% brewer's yeast suspension subcutaneously in rats fasted overnight. The animals were moved into the laboratory one day before the experiment in order to maintain their body temperature constant. On the day of the experiment only animals whose esophageal temperature ranged between 35.5° C. and 37° C. were used. 4 hours after the injection of the brewer's yeast rats with a temperature $\geq$37.5° C. were chosen and split into groups of 7. Suspensions of the test compound were then administered by gavage and the esophageal temperature was recorded 1, 2, 3 and 24 hours after treatment. Results were expressed as "temperature index" which was obtained calculating the total area lying between the temperature curves and a baseline value, corresponding to 36.5° C. Comparisons with controls were performed by the Dunnett test.

The following results obtained are shown in Tables I and II, the compounds being identified as follows:
1. 2-(4-dimethylvinylphenyl)propionic acid (compound of invention)
2. 2-(4-methylvinylphenyl)propionic acid
3. Isaprofen.

TABLE 1

| Activity and Test | 1 | | 2 | | 3 | |
|---|---|---|---|---|---|---|
| | Oral dose mg kg$^{-1}$ | % inhibition | Oral dose mg Kg$^{-1}$ | % inhibition | Oral dose mg Kg$^{-1}$ | % inhibition |
| ANTIINFL-AMMATORY | | | | | | |
| Rat carrag- | | | | | | |

TABLE 1-continued

| Activity and Test | 1 | | 2 | | 3 | |
|---|---|---|---|---|---|---|
| | Oral dose mg kg$^{-1}$ | % inhibition | Oral dose mg Kg$^{-1}$ | % inhibition | Oral dose mg Kg$^{-1}$ | % inhibition |
| ceenan | 3 | 30 | 9 | 16 | 3 | 16 |
| Rat adjuvant arthritis | 9 | 35 | 9 | 13 | 25 | 23 |

TABLE 2

| Activity and Test | 1 | | 2 | |
|---|---|---|---|---|
| | Oral dose mg Kg$^{-1}$ | % inhibition | Oral dose mg Kg$^{-1}$ | % inhibition |
| ANALGESIC | | | | |
| Randall Selitto Test | 25 | 35[a] | 25 | 21[a] |
| | 50 | 75[a] | 50 | 28[a] |
| ANTIPYRETIC | | | | |
| Brewer Yeast pyrexia-rat | 5.00 | 42 | 5 | 13 |

[a] = % pain threshold increase

Tests performed using the Sodium, Calcium, L- and DL-lysine, L- and DL-arginine and N-methyl-D-glucamine salts and methyl, ethyl and pivaloyloxymethyl esters established that these have a level of anti-inflammatory activity which is similar to that of the compound (II) itself.

The invention also provides a pharmaceutical composition comprising 2-(4-dimethylvinylphenyl) propionic acid and/or a physiologically acceptable salt or ester thereof together with a physiologically acceptable carrier or excipient.

The compounds according to the invention may be formulated in conventional manner for administration by any convenient route for example, for oral, rectal, topical, intravenous and intramuscular administration.

For oral administration, the pharmaceutical composition may take the form of, for example, tablets, capsules, powders, solutions, syrups or suspensions prepared by conventional means with physiologically acceptable excipients. We have found that the physiologically acceptable salts of the compound (II) are soluble in water and hence particularly useful for the preparation of compositions for oral administration.

The compounds of the invention may be formulated for rectal administration for example, in the form of suppositories using a conventional suppository excipient. The compositions may also take such forms as creams, ointments and lotions for topical administrations.

Physiologically acceptable salts may be formulated for intravenous or intramuscular administration in dry form for reconstitution before use, or as a sterile solution.

A proposed daily dose for administration to man is 100 mg to 1.6 g e.g. 500 mg to 1 g which may be conveniently administered in two or three doses per day.

The invention is further illustrated by the following Examples. All temperatures are in °C. The abbreviation DMF is used for dimethylformamide. All melting points given are uncorrected.

EXAMPLE 1

2-(4-Dimethylvinylphenyl)Propionic Acid (a) Anhydrous aluminium trichloride (44 g) was slowly added to a stirred solution of fluorobenzene (84.1 g) and isobutyrylchloride (23.4 g) over a period of 30 minutes at a temperature of 10° to 15°. The reaction mixture was refluxed for 3 hours and, after cooling, poured into an ice/concentrated hydrochloric acid mixture. The mass was vigorously stirred and extracted twice with 200 ml portions of ether.

The collected ethereal extracts were washed with two 150 ml portions of a 10% solution of NaOH, then with water and subsequently dried over Na$_2$SO$_4$. The solvent was evaporated and the residue was distilled under reduced pressure to give 4-fluoroisobutyrylbenzene (31.5 g) b.p. 55°–56° C. (4–5 mm). Chemical and structural analyses were consistent with the formula of this product.

(b) Freshly distilled diethylmethylmalonate (62.84 g) was added dropwise to a stirred mixture of sodium hydride (8.86 g) and anhydrous DMF (500 ml) under a slight flow of nitrogen at room temperature.

The mixture was stirred for 30 minutes and treated dropwise with 4-fluoroisobutyrylbenzene (30.4 g). The gaseous flow was stopped and the reaction mixture heated at 115° to 120° for 24 hours. After evaporation of most of the DMF the residue was treated with water (500 ml) and extracted with three 200 ml portions of ether. The combined ethereal extracts were washed twice with 200 ml portions of water and subsequently dried over Na$_2$SO$_4$.

Evaporation of the solvent gave a yellow oily mass which was distilled under reduced pressure (39°–42° C., 5 mm) to leave an oily residue.

(c) The above residue (34 g) was mixed with a solution of NaOH (8 g) in 1:1 methanol:water (140 ml) at room temperature. The stirred solution was heated at 45° to 55° for six hours. After removing methanol (60 ml approx) by evaporation, the cooled mixture was treated with water (200 ml) and extracted twice with 200 ml portions of ether. The aqueous phase was acidified with concentrated hydrochloric acid and again extracted twice with 200 ml portions of ether. The last collected ethereal extracts were dried over Na$_2$SO$_4$ and evaporated to give pure 2-(4-isobutyrylphenyl)propionic acid (21.4 g). The melting point after recrystallisation from ether-ligroin was 78°–80°.

Found: C% 70.75 (Calc. 70.88); H% 7.36 (7.32)

(d) 2-(4-Isobutyrylphenyl)propionic acid (14.4 g) was mixed with a 3% solution of NaOH (320 ml) at room temperature and stirred for 20 minutes until dissolution had occurred, then treated with sodium borohydride (2.6 g) and stirred again for 2 hours. The mixture was extracted twice with 150 ml portions of ether and the aqueous phase was cooled to 0.5°. It was cautiously acidified with dilute hydrochloric acid and again extracted with three 150 ml portions of ether. The collected ethereal extracts were dried over Na$_2$SO$_4$ and evaporated under reduced pressure. The residue was further dried at 60° in a vacuum oven for two hours to give a product (14.4 g). Crystallisation from ethyl acetate gave 2-[4-(1-hydroxy-2-dimethylethyl)phenyl]propionic acid as a white solid m.p. 99°–101°.

(e) A solution of p-toluenesulphonic acid monohydrate (8.4 g) in o-dichlorobenzene (60 ml) was heated at 110° to 120° and treated dropwise with a previously prepared solution of 2-[4-(1-hydroxy-2-dimethylethyl)phenyl]propionic acid (9 g) in o-dichlorobenzene (40 ml) over a period of 20 minutes at the same temperature. The reaction mixture was rapidly cooled to room temperature, poured into water and extracted several times with ether. The combined ethereal extracts were washed with water and then treated with a 5% solution of NaOH. The separated aqueous phase was acidified with a 10% solution of hydrochloric acid and extracted again with ether and the organic phase was separated.

The solvent was removed to give an oily product which was crystallised from ligroin to give the title compound (3.5 g) m.p. 53°–54°.

The residual ligroin solution was chromatographed on an inactivated (10% water) silica gel column (450 g) using a 1,1,1-trichloroethane/ether/methanol mixture (10:3:1) at eluant to give a further 3.5 g of the pure title compound.

Found: C% 76.43 (Calc. 76.44); H% 7.88 (7.90).

EXAMPLE 2

Sodium 2-(4-Dimethylvinylphenyl)Propionate

Stoichiometric amounts of 2-(4-dimethylvinylphenyl)propionic acid and 1 N aqueous sodium hydroxide were stirred at room temperature for 30 minutes. The mixture was washed with 2×50 ml portions of ether and the aqueous solution evaporated to dryness to give the title compound as a white solid, m.p. 166°–168°. I.R. C=O stretch 1550–1560 cm$^{-1}$.

EXAMPLE 3

Calcium-2-(4-Dimethylvinylphenyl)Propionate

Calcium (0.34 g) in 30 ml of anhydrous ethanol was added to a stirred solution of 2-(4-dimethylvinylphenyl)propionic acid (4 g) in 50 ml of ethanol at room temperature. After refluxing for 1 hour, the clear reaction mixture was cooled and maintained at 0° for 10 hours. The title salt was collected by suction filtration and dried under reduced pressure to yield a white crystalline solid (3.85 g) m.p. 120°–122°. I.R. C=O stretch 1550–1560 cm$^{-1}$.

EXAMPLE 4

2-(4-Dimethylvinylphenyl)Propionic Acid, D,L-Lysine Salt

A solution of DL-lysine (7.17 g) in 30 ml water was added to a solution of 2-(4-dimethylvinylphenyl) propionic acid (10 g) in ethanol (100 ml) at room temperature. The reaction mixture was refluxed for 2 hours, cooled and treated with activated charcoal until clear. The solvent was partially removed under vacuum and the title salt precipitated by addition of acetone, to give a crystalline powder (12.7 g) which was dried at 50° in a vacuum stove for 2 hours. m.p. 175°–177°.

The experiment was repeated using L-lysine in place of D,L-lysine to obtain the L-lysine salt, m.p. 154°–158°. I.R. Both salts showed the disappearance of the characteristic NH stretching band of the free NH$_2$ group at 3350 cm$^{-1}$.

EXAMPLE 5

2-(4-Dimethylvinylphenyl)Propionic Acid, D,L-Arginine Salt

A saturated solution of DL-arginine (4.26 g) in water was added to a stirred solution of 2-(4-dimethylvinylphenyl)propionic acid (5 g) in acetone (20 ml) and water (5 ml). After stirring for 1 hour at room temperature the solvent was removed and the residue crystallized from acetone-ethanol to yield the title compound (8.25 g) m.p. 187°–189° C.

The experiment was repeated using L-arginine in place of D,L-arginine to yield the L-arginine salt as an amorphous solid. m.p. 105°–107° I.R. Both salts showed the disappearance of the characteristic NH stretching band of the free NH$_2$ group at 3350 cm$^{-1}$.

EXAMPLE 6

2-(4-Dimethylvinylphenyl)Propionic Acid, N-Methyl-D-Glucamine Salt

A solution of 2-(4-dimethylvinylphenyl)propionic acid (3 g) and N-methyl-D-glucamine (2.86 g) in anhydrous ethyl alcohol (35 ml) was refluxed for 1 hour. The solvent was partially removed under vacuum and the title salt precipitated by addition of acetone to yield a crystalline product (3 g) which was dried at 50° in a vacuum stove for 1 hour. m.p. 128°–130° C. I.R. C=O stretch 1550–1560 cm$^{-1}$.

EXAMPLE 7

2-(4-Dimethylvinylphenyl)Propionic Acid (a) Freshly distilled diethylmethylmalonate (80 ml) was added dropwise to a stirred mixture of sodium hydride (13.4 g) and anhydrous DMF (170 ml) under a slight flow of nitrogen at room temperature. The mixture was stirred for 30 minutes and treated dropwise with 4-fluoroisobutyrylbenzene (58 g) prepared as in Example 1. The gaseous flow was stopped and the reaction mixture heated at 118°–120° for 24 hours. After evaporation of most of the DMF, the residue was treated with water (100 ml) and then evaporated to remove all the DMF. The residue was hydrolysed with a solution of NaOH (40.5 g) in water (1.1 l) and methanol (200 ml), and the resulting mixture boiled and stirred for 5 hours and then concentrated by evaporation of 360 ml of solvent.

The aqueous solution was then extracted twice with 120 ml portions of methylene chloride. A freshly prepared solution of sodium borohydride in 2% NaOH was added dropwise over 30 minutes to the aqueous solution at room temperature and stirred for 2 hours. It was cautiously acidified with concentrated hydrochloric acid (130 ml) and then concentrated to half volume.

The solution of 10 N NaOH was added to reach a pH value of about 6 and the mixture extracted with ethyl acetate (3×200 ml). Evaporation of the solvent gave 51 g of crude 2-[4-(1-hydroxy-2-dimethylethyl)phenyl] propionic acid.

(b) A solution of the acid (51 g) prepared in (a) in anhydrous methanol (160 ml) was added dropwise to a boiling solution of p-toluenesulphonic acid (27 g) in o-dichlorobenzene (400 ml) and methanol (160 ml). The methanol was distilled off and the solution was heated for 45 minutes at 110°. The reaction mixture was rapidly cooled to room temperature and treated with a solution of NaHCO$_3$. (35 g) in water (400 ml).

The upper phase was separated and the water phase was extracted twice with methylene chloride (50 ml×2).

The combined organic phases were washed with water and after evaporation of the solvent the residue was distilled under reduced pressure (105°; 0.6 mm) to yield 35 g. of the title compound, methyl ester.

A solution of NaOH (10 g) in methanol (ml 150) and water (370 ml) was added to the ester and the resulting mixture was boiled for 3 hours. The methanol was evaporated, the cooled mixture was extracted with methylene chloride, and the separated water phase acidified with dilute HCl until pH 3 and then extracted with methylene chloride (4×100 ml). After evaporation of the organic phase the residue was crystallized from ligroin to give the title compound (25 g) m.p. 55°–56°.

EXAMPLE 8

2-(4-Dimethylvinylphenyl)Propionic Acid, Ethyl Ester

A solution of 2-(4-dimethylvinylphenyl)propionic acid (11.5 g) in anhydrous ethanol (250 ml) and 2.5 ml of 98% $H_2SO_4$ was refluxed for 4 hours. After cooling the solvent was removed and the oily residue was treated with a saturated $NaHCO_3$ solution, extracted with two 100 ml portions of ether and dried over $Na_2SO_4$. Evaporation of the solvent gave a white oil which was dried at 40° in a vacuum stove for 3 hours to yield the title ester (12.5 g) as an oily product. Found: C% 75.65 (Calc 75.44); H% 8.62 (8.42).

EXAMPLE 9

2-(4-Dimethylvinylphenyl)Propionic Acid, Methyl Ester

The title compound was prepared according to the method of Example 8 except that methanol, not ethanol, was reacted with the starting acid to yield an oily product. Found: C% 76.87 (Calc. 77.03); H% 8.22 (8.31).

EXAMPLE 10

2-(4-Dimethylvinylphenyl)Propionic Acid, Pivaloyloxymethyl Ester

A solution of sodium 2-(4-dimethylvinylphenyl)propionate (3 g) and chloro-methyl pivalate (3.9 g) in toluene (50 ml) was refluxed for 6 hours. After cooling, 50 ml of ethyl ether were added and the mixture was washed with 10% $NaHCO_3$. The solvent was removed, and the residue dried at 60° for 3 hours in a vacuum stove to yield the title ester as an oily product (2 g). Found: C% 71.5 (Calc. 71.66); H% 8.2 (8.23).

| PHARMACEUTICAL EXAMPLES: | |
|---|---|
| TABLETS | mg/tablet |
| (i) | |
| Active ingredient | 250.0 |
| Lactose | 101.9 |
| Maize Starch | 49.5 |
| Pregelatinised Maize Starch | 27.0 |
| Polyvinyl Pyrrolidone | 3.6 |
| Sodium Carboxymethylcellulose | 13.5 |
| Colloidal Silicon dioxide | 4.5 |
| Weight | 450.0 |
| (ii) | |
| Active ingredient | 250.0 |
| Microcrystalline cellulose | 93.0 |
| Colloidal Silicon dioxide | 3.5 |
| Magnesium Stearate | 3.5 |
| Weight | 350.0 |

| -continued | |
|---|---|
| PHARMACEUTICAL EXAMPLES: | |
| CAPSULES | mg/capsule |
| Active ingredient | 250.0 |
| Microcrystalline cellulose | 93.0 |
| Colloidal Silicon dioxide | 3.5 |
| Magnesium Stearate | 3.5 |
| Fill Weight | 350.0 |
| SUPPOSITORIES | mg/suppository |
| Active ingredient | 500.0 |
| Suppository base* | 2500.0 |
| Weight | 3000.0 |
| injections | |
| Active ingredient 200 mg | |
| Water for injections B.P. to 2 ml. | |

*Any conventional base may be used.

Sodium chloride may be added to adjust the tonicity of the solution.

The active ingredient in each of the above examples is 2-(4-dimethylvinylphenyl)propionic acid.

We claim:

1. 2-(4-Dimethylvinylphenyl)propionic acid of formula (II):

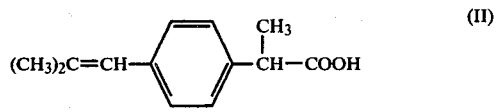

and physiologically acceptable salts thereof selected from the group consisting of alkali metal salts, alkaline earth metal salts, lysine, arginine and N-methyl-glucamine salts, and physiologically acceptable esters selected from the group consisting of $C_{1-4}$ alkyl esters and $C_{2-5}$ alkanoyloxy methyl esters.

2. 2-(4-Dimethylvinylphenyl)propionic acid.

3. A compound according to claim 1 which is selected from the group consisting of calcium and DL-lysine salts.

4. A process for the preparation of 2-(4-Dimethylvinylphenyl)-propionic acid of formula II or a physiologically acceptable ester thereof as defined in claim 1 which comprises dehydrating a compound of formula III:

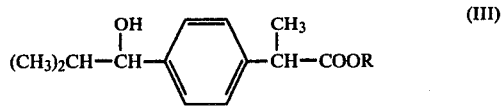

wherein R is a hydrogen atom or a $C_1$–$C_4$ alkyl group or an alkanoyloxymethyl group, using p-toluene sulphonic acid, a derivative thereof, or sulphuric acid, in a high boiling inert solvent at an elevated temperature.

5. A process for the preparation of a compound according to claim 1, which comprises dehydrating a compound of formula:

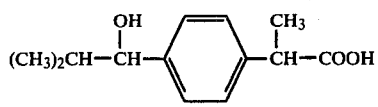

using p-toluene sulphonic acid or a derivative thereof, or sulphuric acid in a high boiling inert solvent at an elevated temperature in the presence of a $C_1$–$C_4$ alkanol to produce an ester of formula (IV):

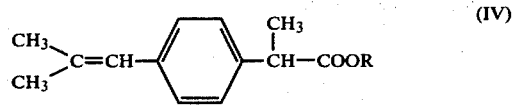

wherein R is a $C_1$–$C_4$ alkyl group.

6. A process as claimed in claim 4, wherein an acid of formula II is obtained, which acid is reacted with an appropriate base to form a physiologically acceptable alkali metal salt, alkaline earth metal salt, lysine, arginine or N-methyl-glucamine salt thereof.

7. A process as claimed in claim 5 wherein the ester of formula (IV) is hydrolized to the corresponding acid.

8. A process as claimed in claim 7, wherein the acid is reacted with an appropriate base to form a physiologically acceptable alkali metal salt, alkaline earth metal salt, lysine, arginine or N-methyl-glucamine salt.

9. A pharmaceutical composition which comprises as active ingredient 2-(4-dimethylvinylphenyl) propionic acid, a physiologically acceptable ester or salt as defined in claim 1, or mixtures thereof together with a physiologically acceptable carrier or excipient.

10. A pharmaceutical composition according to claim 9, formulated for oral administration.

11. A pharmaceutical composition according to claim 9 or 10 in unit dosage form and containing from about 30 mg to about 800 mg of active ingredient.

12. A method for the treatment of a patient suffering from pain which comprises administering to the patient an effective amount of a compound of formula (II) as defined in claim 1.

* * * * *